United States Patent
Bourgeois et al.

Patent Number: 6,126,611
Date of Patent: Oct. 3, 2000

[54] APPARATUS FOR MANAGEMENT OF SLEEP APNEA

[75] Inventors: Ivan Bourgeois, Verviers, Belgium; Richard Sutton, London, United Kingdom

[73] Assignee: Medtronic, Inc., Minneapolis, Minn.

[21] Appl. No.: 09/239,014

[22] Filed: Jan. 29, 1999

[30] Foreign Application Priority Data

Feb. 4, 1998 [GB] United Kingdom .................. 9802382

[51] Int. Cl.⁷ ...................................................... A61B 5/04
[52] U.S. Cl. ........................ 600/529; 600/508; 600/509; 607/4; 607/42
[58] Field of Search ..................... 600/529, 508, 600/483, 531, 532, 533, 538, 484, 509, 526, 528, 510; 607/4, 5, 7, 9, 11, 18, 42

[56] References Cited

U.S. PATENT DOCUMENTS

| | | |
|---|---|---|
| 4,596,251 | 6/1986 | Plicchi et al. . |
| 4,769,032 | 9/1988 | Steinberg . |
| 4,901,725 | 2/1990 | Nappholz et al. . |
| 5,002,566 | 3/1991 | Carpentier et al. . |
| 5,335,657 | 8/1994 | Terry, Jr. et al. ........................ 607/45 |
| 5,443,446 | 8/1995 | Shturman . |
| 5,540,732 | 7/1996 | Testerman . |
| 5,974,340 | 10/1999 | Kadhiresan ............................ 607/18 |

OTHER PUBLICATIONS

"Bradycardia during Sleep Apnea," C. Zwillich, et al. (J. Clin. Invest., vol. 69, Jun. 1982, pp. 1286–1292).

"Relationship of Ventricular Ectopy to Oxyhemoglobin in Patients with Obstructive Sleep Apnea," J. Shepard Jr., et al. (Chest, 88/3 Sep. 1985, pp. 335–340).

"Cyclical Variation of the Heart Rate in Sleep Apnea Syndrome, Mechanisms, and Usefulness of 24 h Electrocardiography as a Screening Technique," C. Guilleminault, et al. (The Lancet, Jan. 21, 1984, pp. 126–131).

"Changes in Heart Rate during Obstructive Sleep Apnoea," S. Andreas, et al. (Eur. Respir. J., 1992, 5, pp. 853–857).

*Primary Examiner*—Cary O'Connor
*Assistant Examiner*—Navin Natnithithadna
*Attorney, Agent, or Firm*—Thomas F. Woods; Michael J. Jaro; Harold Patton

[57] ABSTRACT

A device for treating sleep apnea comprising means for detecting an apnea event and means responsive to detection of an apnea event for stimulating the heart at a higher rate than the heart's natural rate.

14 Claims, 3 Drawing Sheets

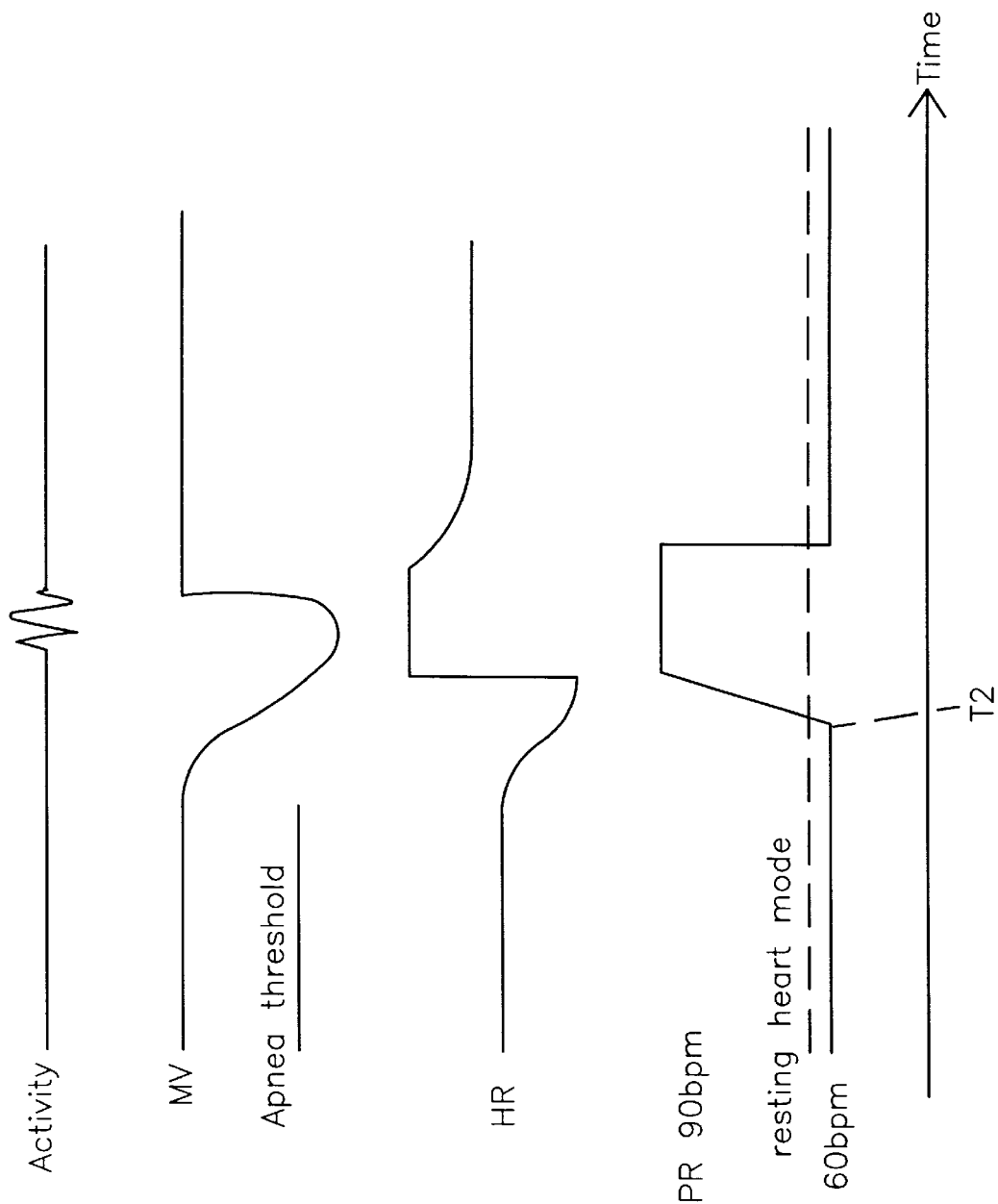

APPARATUS FOR MANAGEMENT OF SLEEP APNEA

FIELD OF THE INVENTION

This invention relates to an apparatus for management of sleep apnea.

BACKGROUND OF THE INVENTION

Sleep apnea has been known for some time as a medical syndrome in two generally recognized forms. The first is central sleep apnea, which is associated with the failure of the body to automatically generate the neuro-muscular stimulation necessary to initiate and control a respiratory cycle at the proper time. Work associated with employing electrical stimulation to treat this condition is discussed in Glenn, "Diaphragm Pacing: Present Status", Pace, V. I, pp 357–370 (July–September 1978).

The second sleep apnea syndrome is known as obstructive sleep apnea. Ordinarily, the contraction of the dilator muscles of the upper airways (nose and pharynx) allows their patency at the time of inspiration. In obstructive sleep apnea, the obstruction of the airways results in a disequilibrium between the forces which tend to their collapse (negative inspiratory transpharyngeal pressure gradient) and those which contribute to their opening (muscle contraction). The mechanisms which underlie the triggering of obstructive apnea include a reduction in the size of the superior airways, an increase in their compliance, and a reduction in the activity of the dilator muscles. The dilator muscles are intimately linked to the respiratory muscles and these muscles respond in a similar manner to a stimulation or a depression of the respiratory centre. The ventilatory fluctuations observed during sleep (alternately hyper and hypo ventilation of periodic respiration) thus favour an instability of the superior airways and the occurrence of oropharyngeal obstruction. The respiratory activation of the genioglossus has been particularly noted to be ineffective during sleep. The cardiovascular consequences of apnea include disorders of cardiac rhythm (bradycardia, auriculoventricular block, ventricular extrasystoles, tachyarrhythmias) and hemodynamic (pulmonary and systemic hypertension). This results in a stimulatory effect on the autonomic nervous system. The electroencephalographic awakening is responsible for the fragmentation of sleep. The syndrome is therefore associated with an increased morbidity (the consequence of diurnal hypersomnolence and cardiovascular complications).

A method for treatment of obstructive sleep-apnea syndrome is to generate electrical signals to stimulate those nerves which activate the patient's upper airway muscles in order to maintain upper airway patency. For example, in U.S. Pat. No. 4,830,008 to Meer, inspiratory effort is monitored and electrical signals are directed to upper airway muscles in response to the monitored inspiratory effort. In U.S. Pat. No. 5,123,425 a collar contains a sensor to monitor respiratory functioning to detect an apnea episode and an electronics module which generates electrical bursts to electrodes located on the collar. The electrical bursts are transferred transcutaneously from the electrodes to the nerves innervating the upper airway muscles. In U.S. Pat. No. 5,174,287 issued to Kallok, sensors monitor the electrical activity associated with contractions of the diaphragm and also the pressure within the thorax and the upper airway. Whenever electrical activity of the diaphragm suggests that an inspiration cycle is in progress and the pressure sensors show an abnormal pressure differential across the airway, the presence of obstructive sleep apnea is assumed and electrical stimulation is applied to the musculature of the upper airway. In U.S. Pat. No. 5,178,156 issued to Wataru et al, respiration sensing includes sensors for sensing breathing through left and right nostrils and through the mouth which identifies an apnea event and thereby triggers electrical stimulation of the genioglossus. In U.S. Pat. No. 5,190,053 issued to Meer, an intra-oral, sublingual electrode is used for the electrical stimulation of the genioglossus to maintain the patency of an upper airway. In European Application No. 0507580 (Kallok et al), upon sensing of the onset of an apnea event, a stimulation generator provides a signal for stimulating the muscles of the upper airway at a varying intensity such that the intensity is gradually increased during the course of the stimulation.

In the known systems, it has been found difficult to ensure stimulation of the correct muscular structures in the upper airway in each patient for example, the hypoglossal nerve is close to other structures which should not be stimulated. Further, an electrode intended to stimulate the hypoglossal nerve must be placed through a tiny incision which makes anatomical identification difficult and airflow measurements impossible.

As an alternative, several self-sizing cuff, or half-cuff designs have been proposed (see e.g. U.S. Pat. Nos. 4,573,481; 4,602,624; 5,095,905 and 5,344,438). Even with such designs, however, the surgeon implanting the electrode needs to be able to place the electrode precisely at the point on the nerve where effective stimulation can be applied to open the airway.

SUMMARY OF THE INVENTION

The present invention aims to overcome these problems by providing a device for treating sleep apnea comprising means for detecting an apnea event and means responsive to detection of an apnea event for stimulating the heart at a higher rate than the heart's natural rate.

The invention, according to another aspect, provides a method of treating sleep apnea comprising detecting apnea and, in response to such detection, pacing the heart at a higher rate.

The inventors have noted that patients with implanted fixed rate (i.e. 70 bpm) cardiac pacemakers often suffer from insomnia. It was realised that high rate of cardiac pacing often alter the patient's sleep pattern, sometimes even causing the patient to wake. The present invention aims to use this clinical effect to positive effect in treating sleep apnea.

The invention involves detecting sleep apnea, as discussed further below, and in response to such detection, applying pacing pulses to the heart at an otherwise non-physiologically high rate i.e. a higher rate that needed but below pathological rates.

During sleep, the heart typically beats at 30–55 bpm. In the preferred embodiment of the present invention, on detection of sleep apnea, pacing pulses at a rate of 70–100 bpm are delivered to the heart. This cardiac pacing rate may be achieved gradually or by an abrupt increase.

During sleep, such a high pacing rate would tend to arouse or awaken the patient. This would end the apnea and allow the patient to breath.

Preferred embodiments of the present invention will now be described, in more detail, with reference to the accompanying drawings.

BRIEF DESCRIPTION OF THE DRAWINGS

FIG. 3 shows waveforms of heart rate and respiratory rate over time, indicating the occurrence of an apnea event.

DETAILED DESCRIPTION OF THE DRAWINGS

Figure 1:
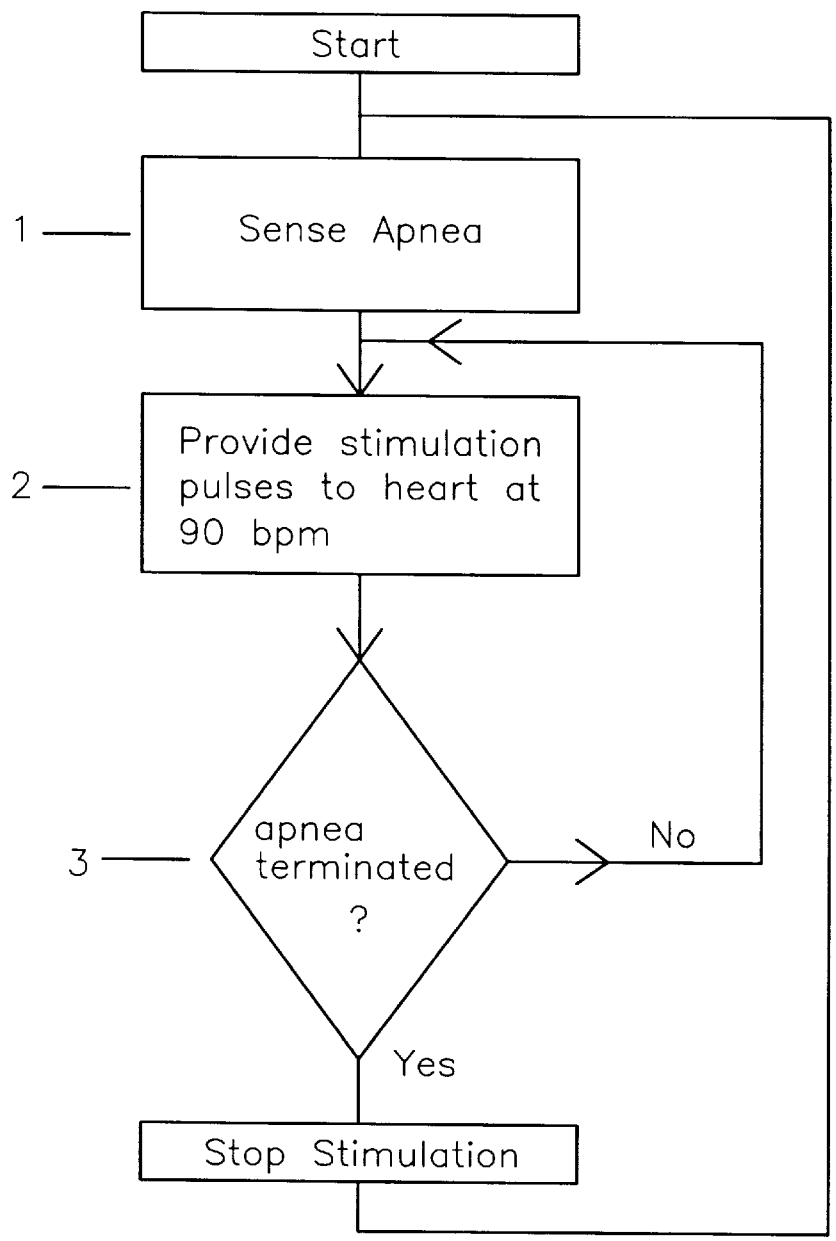
FIG. 1 is a flow chart of the operation of a device according to the present invention.

The preferred embodiment detects low cardiac rates as an indication of resting. Preferably, the invention uses a typical rate-responsive bradycardia pacemaker and transvenous medical electrical lead which, upon detection of sleep apnea and suspension of respiration during sleep, would pace the heart at a relatively higher frequency.

Sleep apnea is often associated with bradycardia. In one embodiment, therefore, a low heart rate, below a predetermined apnea threshold, detected by a known bradycardia detection system, may be used as an indication of sleep apnea. Such a predetermined apnea threshold, incidentally, is preferably set or programmed by the physician. Thus, detection of a decrease in heart rate below the preset threshold, by the bradycardia pacemaker could also be a trigger for rapid rate pacing which acts to alter the sleep pattern of the patient.

Instead of using detection of low heart rate as an indication of sleep apnea, there are other readily detectable physiological phenomena present when an alteration in sleep level is highly desirable. Other detection schemes such as minute ventilation or respiration rate, as used in the pacemaker described in U.S. Pat. No. 4,901,725, or pressure or impedance sensing, may be used. These additional detection schemes, moreover, may be used alone or in conjunction with all other schemes. Moreover, each may feature a pre-determined threshold, programmable by the physician. If apnea is detected, it should be determined whether or not there is a low heart rate.

Once triggered by detection of low cardiac rate, minute ventilation or respiratory rate, the pacing system of the present invention would begin to pace rapidly, e.g. 90 bpm. Many different pacing modes are available, all of which could be used in the present invention. It is expected that VVI pacing could be most effective.

Referring now to the drawings, preferred embodiments will now be described.

The invention may be used in patients who already have an implanted pacemaker or may be implanted into patients specifically to treat sleep apnea. If a patient is already fitted with a pacemaker, e.g. to treat bradycardia, the pacemaker will be already programmed to pace at a given, normal rate. The pacemaker may need to be programmed according to the present invention.

In any case, the device is arranged to sense an apnea event. In one embodiment a decrease in heart rate below a given threshold is taken as an indication of the onset of sleep apnea. Devices are known which detect a decrease in heart rate and, in response to a detected decrease, activate a pulse generator. One such device is the bradycardia pacemaker shown in FIG. 2.

Lead 14 includes an intracardiac electrode 24 located near its distal end and positioned within the right ventricle 16. Electrode 24 is coupled by a lead conductor 14 through an input capacitor 26 to the node 28, and to the input/output terminals of an input/output circuit 30.

Similarly, the lead 15 has a distally located intracardiac electrode positioned within the right atrium 17. Electrode 22 is coupled by a lead conductor 15 through an input capacitor 75 to a node 76, and to the input/output terminals of the input/output circuit 30.

Input/Output Circuit 30 contains the operating input and output analog circuits for digital controlling and timing circuits necessary for the detection of electrical signals derived from the heart, such as the cardiac electrogram, output from sensors (not shown) connected to the leads 14 and 15, as well as for the application of stimulating pulses to the heart to control its rate as a function thereof under the control of software-implemented algorithms in a Microcomputer Circuit 32.

Microcomputer Circuit 32 comprises an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components.

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external programmer (not shown), is accomplished in the preferred embodiment by means of all data first being digitally encoded and then pulse position modulated on a damped RF carrier, as substantially described in U.S. Pat. No. 5,127,404, issued on Jul. 7, 1992, entitled "Telemetry Format for Implantable Medical Device". A reed switch 51 is connected to Input/Output Circuit 30 to enable patient follow-up via disabling the sense amplifier 146 and enabling telemetry and programming functions, as is known in the art.

A Crystal Oscillator Circuit 56, typically a 32,768 Hz crystal-controlled oscillator, provides main timing clock signals to Digital Controller/Timer Circuit 50. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating commands for controlling the timing of the pacemaker are coupled by bus 48 to Digital Controller/Timer Circuit 50 wherein digital timers set the overall escape interval of the pacemaker, as well as various refractory, blanking and other timing windows for controlling the operation of the peripheral components within Input/Output Circuit 50.

Digital Controller/Timer Circuit 50 is coupled to sense amplifiers (SENSE) 64 and 67, and to electrogram (EGM) amplifiers 66 and 73 for receiving amplified and processed signals pickup up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device".

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art.

In a preferred embodiment of the present invention, pacemaker 10 is capable of operating in various non-rate-responsive modes which include DDD, DDI, VVI, VOO, AOO, VDD. DVI, AAT and VVT, as well as corresponding rate-responsive modes of DDDR, DDIR, VVIR, VOOR and VVTR. Further, pacemaker 10 can be programmably configured to operate such that it varies its rate only in response to one selected sensor output, or in response to both sensor outputs, if desired.

Alternatively, apnea could be sensed by monitoring inspiratory effort as in e.g. U.S. Pat. No. 4,830,008 to Meer, or monitoring respiratory functioning as in e.g. U.S. Pat. No. 5,123,425. Another method of detecting apnea, as described in U.S. Pat. No. 5,174,287 to Kallok involves monitoring the electrical activity associated with contractions of the diaphragm and also pressure within the thorax and the upper airway. In U.S. Pat. No. 5,178,156 to Wataru et al respiration sensing includes sensors for sensing breathing through left and right nostrils and through the mouth to identify an apnea event.

U.S. Pat. No. 5,201,808 to Steinhaus et al; U.S. Pat. No. 5,271,395 to Wahlstrand et al and U.S. Pat. No. 4,596,251 to Plicchi et al disclose impendence sensors such as those used in measuring minute volume for control of output rate of cardiac pacemakers, which can be used to provide a respiratory effort sensor to identify apnea. U.S. Pat. No. 5,540,732 to Testerman also discloses a method of detecting sleep apnea using an impedance sensor. Many other methods of detecting sleep apnea, such as disclosed in EP 0702978 and EP 0706808, are known and may be used in the present invention.

In response to the detection of sleep apnea in Step 1 of FIG. 1, the stimulation device applies pacing pulses at a higher than normal rate, e.g. 90 bpm, to the heart (Step 2).

Figure 2:
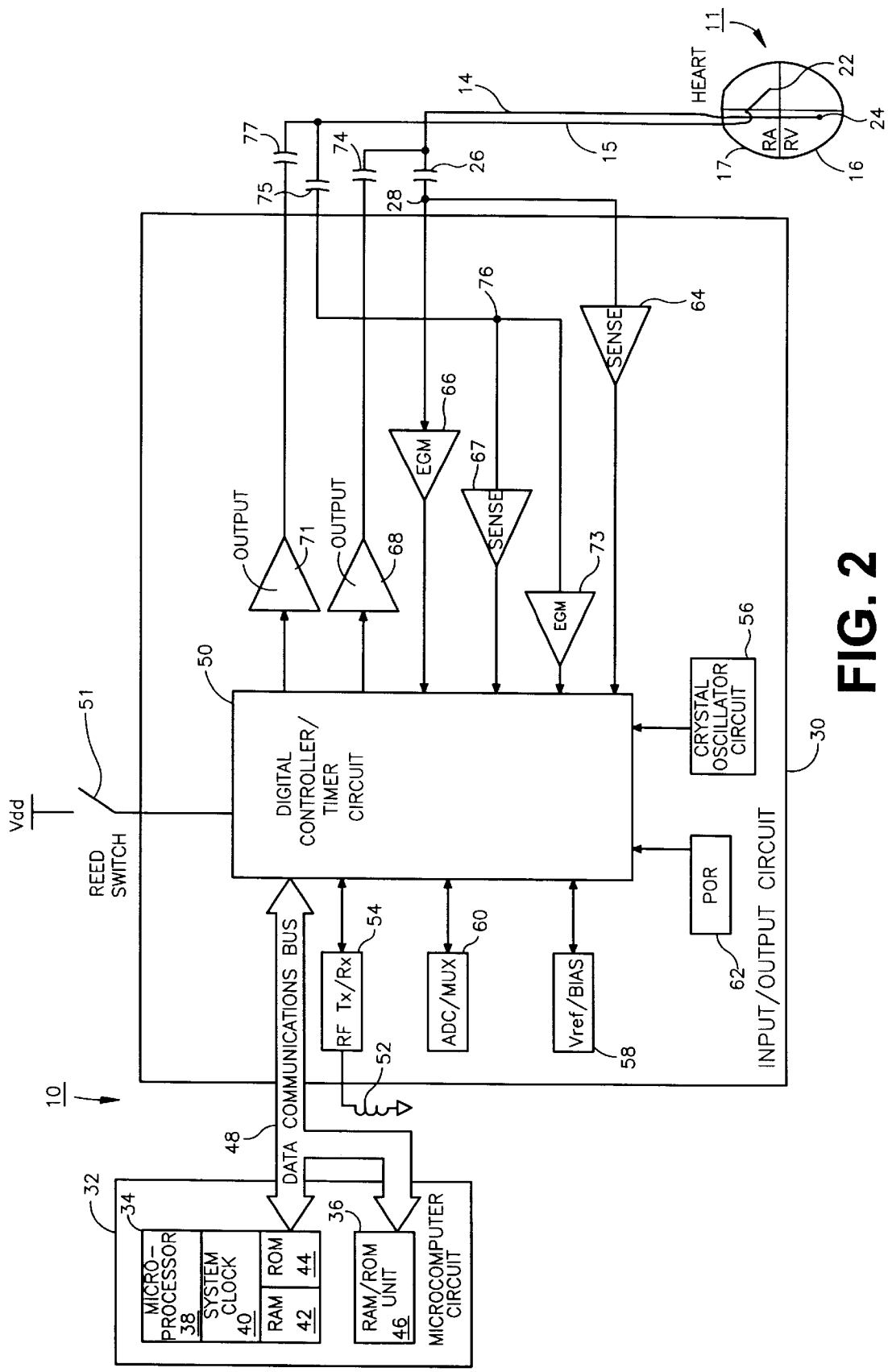
FIG. 2 is a block diagram of a cardiac stimulator which may be used in the present invention.

The high rate pacing pulses may be generated and applied to the heart using the device shown in FIG. 2, as described above. Of course, many other types of pacing systems are known, and any may be used in the present invention.

In a preferred embodiment, the device is provided with an on/off switch mechanism (such as a reed switch) for connecting/disconnecting the apnea circuit.

In one arrangement, for example where apnea is detected through minute ventilation, if the apnea persists for a predetermined time, e.g. 10 seconds, the cardiac pacing rate switches to the higher rate. This mode switch can be abrupt or gradual. After a fixed period of time, or when the apnea is terminated, pacing is then withdrawn.

The patient has to switch the mode switch mechanism on with a magnet when going to sleep and switch it off when he wakes up. (This function is opposite to that for VVIR pulse generation). If the pulse generator has an activity sensor, switching can automatically occur if body activity less than a pre-determined threshold or minute ventilation indicative of sleep is detected for a predetermined time, e.g. 10 seconds. If body activity is subsequently detected over a period of say a few seconds, the pulse generator then switches back to its normal operation.

In an alternative arrangement, the mode switch is triggered when arterial or venus oxygen saturation drops below a predetermined level in the absence of any minute ventilation. This predetermined level could be a fixed level or a combination of oxygen saturation decay and a set level.

An on/off switch could, alternatively, be triggered by, e.g. a pressure sensor in the thorax as disclosed in, e.g., U.S. Pat. No. 5,540,732 to Testerman.

The unusually high paced heart rate will cause the patient to wake and this should terminate the apnea event (Step 3).

FIG. 3 shows the effect of the present invention on the heart rate and respiratory rate of a patient. The top waveform shows the activity of the patient overtime. The next waveform down shows minute ventilation over time, with a predetermined apnea threshold indicated.

The third waveform down shows the patient's heart rate over time and the bottom waveform shows the patient's pacing rate over time, with the dotted line indicating the patient's resting heart rate. The waveforms shown relate to those for a patient already having an implanted cardiac pacer set to pace at a first, lower pacing rate, e.g. 60 bpm. This rate is selected to be less than the patient's resting heart rate so as not to apply pacing therapy while the patient is merely resting.

At time D2, the minute ventilation decreases below the apnea threshold. This decrease in respiratory rate, indicative of an apnea event, also results in a decrease in heart rate, as shown. In response to this detection, corresponding to detection of an apnea event, a higher pacing rate, e.g. 90 bpm is applied by the pacer. The increased pacing rate results in an increasing heart rate.

The apnea is thus quickly terminated and the pacing at the high rate of 90 bpm is terminated resulting in the heart rate returning to the resting rate.

The feature of activity sensing is an optional feature.

Once the apnea is terminated, the device returns to its standby mode, ready to detect another apnea event. If the patient also uses the pacemaker for treating brady- or tachyarrhythmias, the pacer will return to pacing at the pre-programmed lower (normal) rate.

What is claimed is:

1. An implantable system for treating sleep apnea comprising:
   implantable means for sensing sleep apnea; and
   implantable means for electrically stimulating the heart in response to the sensing of sleep apnea.

2. A system for treating sleep apnea according to claim 1, wherein the means for detecting sleep apnea comprises means for sensing the minute ventilation of a patient.

3. A system for treating sleep apnea according to claim 2, wherein the means for sensing minute ventilation further comprises means for sensing a predetermined apnea minute ventilation threshold.

4. A system for treating sleep apnea according to claim 1, wherein the means for detecting sleep apnea comprises means for sensing the respiration rate of a patient.

5. A system for treating sleep apnea according to claim 1, wherein the means for detecting sleep apnea comprises means for sensing an apnea-indicative heart rate of a patient.

6. A system for treating sleep apnea according to claim 2, 3 or 4, wherein the means for sensing sleep apnea further comprises an activity sensor.

7. A system for treating sleep apnea according to claim 1, wherein the means for electrically stimulating the heart comprises means for electrically stimulating the heart of a patient at a rate which is higher than the otherwise physiologic rate of the patient.

8. A system for treating sleep apnea according to claim 7, wherein the rate which is higher than the otherwise physiologic rate of the patient is greater than 90 beats per minute.

9. A system for treating sleep apnea according to claim 1, wherein the means for electrically stimulating the heart comprises means for detecting the present physiologic heart rate of the patient and stimulating the patient's heart for a preset period of time.

10. A system for treating sleep apnea according to claim 1, wherein the means for electrically stimulating the heart further comprises a medical electrical lead.

11. A system for treating sleep apnea according to claim 10, wherein the means for electrically stimulating the heart further comprises a transvenous medical electrical lead.

12. A system for treating sleep apnea according to claim 1, further comprising mode switching means for switching the system from a first mode in which apnea is detected to a second mode in which apnea is not detected.

13. A system for treating sleep apnea according to claim 12, wherein the mode switching means comprises a reed switch.

14. A system for treating sleep apnea according to claim 12, wherein the mode switching means is triggered by an activity sensor sensing less than a predetermined activity level.

* * * * *